(12) United States Patent
Hessenberger et al.

(10) Patent No.: US 11,807,399 B2
(45) Date of Patent: Nov. 7, 2023

(54) CUSHION FOR AN AIRCRAFT SEAT, HAVING INTEGRATED SENSOR ELECTRONICS

(71) Applicant: NEVEON Austria GmbH, Kremsmünster (AT)

(72) Inventors: Norbert Hessenberger, Ohlsdorf (AT); Christoph Zipko, Wels (AT); DI Klaus Brenner, Engerwitzdorf (AT)

(73) Assignee: NEVEON Austria GmbH, Kremsmüns Ter (AT)

( * ) Notice: Subject to any disclaimer, the term of this patent is extended or adjusted under 35 U.S.C. 154(b) by 108 days.

(21) Appl. No.: 17/441,363

(22) PCT Filed: Mar. 20, 2020

(86) PCT No.: PCT/EP2020/057793
§ 371 (c)(1),
(2) Date: Sep. 21, 2021

(87) PCT Pub. No.: WO2020/193411
PCT Pub. Date: Oct. 1, 2020

(65) Prior Publication Data
US 2022/0177162 A1     Jun. 9, 2022

(30) Foreign Application Priority Data
Mar. 22, 2019 (DE) .................. 10 2019 203 979.0

(51) Int. Cl.
*B64F 5/40*     (2017.01)
*B64D 11/06*     (2006.01)

(52) U.S. Cl.
CPC ............ *B64F 5/40* (2017.01); *B64D 11/0647* (2014.12)

(58) Field of Classification Search
CPC ... B64F 5/40; B64D 11/0647; B64D 11/0607; A61B 5/18; B60N 2/002; B60N 2/70
(Continued)

(56) References Cited

U.S. PATENT DOCUMENTS 6,395,121 B1    5/2002    De Bastiani
10,118,514 B2    11/2018    Obadia et al.
(Continued)

FOREIGN PATENT DOCUMENTS

AT         502289 A1    2/2007
DE      19961874 C1    7/2001
(Continued)

OTHER PUBLICATIONS

Mlakar et al., "Design Investigation of Embroidered Interactive Elements on Non-Wearable Textile Interfaces", Media Interaction Lab, University of Applied Sciences Upper Austria, COMET Project TextileUX, 2020, 10 pages.

*Primary Examiner* — Mark R Wendell
(74) *Attorney, Agent, or Firm* — THE WEBB LAW FIRM (57) ABSTRACT

In a first aspect, provided is a cushion for an aircraft seat including at least one cushion having an upper side and a lower side of at least one plastic foam; at least one sensor system, where at least one sensor system is arranged in a region of the cushion adjacent the bottom surface of the cushion; and at least one flame retardant fabric covering at least one side of the at least one cushion. In a second aspect, provided is a cushion for an aircraft seat including at least one pad made of at least one plastic; at least one stabilizing means embedded in the at least one plastic; and at least one sensor system arranged on the at least one stabilizing means.

17 Claims, 9 Drawing Sheets

(58) Field of Classification Search
USPC .................................................... 297/217.2
See application file for complete search history.

(56) References Cited

U.S. PATENT DOCUMENTS

| | | | |
|---|---|---|---|
| 10,176,694 | B2 | 1/2019 | Sharma |
| 10,647,434 | B2 | 5/2020 | Hessenberger |
| 11,220,342 | B2 * | 1/2022 | Erb .................. B60N 2/0284 |
| 2007/0123129 | A1 | 5/2007 | Moseneder |
| 2007/0200721 | A1 | 8/2007 | Stanley et al. |
| 2008/0238159 | A1 | 10/2008 | Parnis et al. |
| 2010/0109390 | A1 | 5/2010 | Nishimura et al. |
| 2010/0244540 | A1 | 9/2010 | Leponce et al. |
| 2011/0221453 | A1 | 9/2011 | Hwang et al. |
| 2014/0039330 | A1 | 2/2014 | Seo et al. |
| 2018/0056814 | A1 | 3/2018 | Tanyi |
| 2018/0281621 | A1 | 10/2018 | Kaku et al. |
| 2018/0319290 | A1 | 11/2018 | Wawrok et al. |
| 2019/0175114 | A1 * | 6/2019 | Gallagher ............ A61B 5/0006 |
| 2020/0108936 | A1 | 4/2020 | Erb et al. |
| 2021/0086721 | A1 | 3/2021 | Carraro et al. |
| 2021/0114332 | A1 | 4/2021 | Hessenberger |

FOREIGN PATENT DOCUMENTS

| | | |
|---|---|---|
| DE | 102004037913 A1 | 3/2006 |
| DE | 102012111859 A1 | 2/2014 |
| DE | 102015014014 A1 | 5/2017 |
| DE | 102017113037 A1 | 10/2018 |
| EP | 2155515 B1 | 10/2012 |
| EP | 3141482 A1 | 3/2017 |
| WO | 0045674 A1 | 8/2000 |
| WO | 2013096985 A2 | 7/2013 |
| WO | 2015075671 A1 | 5/2015 |
| WO | 2017135263 A1 | 8/2017 |
| WO | 2017144662 A1 | 8/2017 |
| WO | 2018177808 A1 | 10/2018 |
| WO | 2019010473 A1 | 1/2019 |

* cited by examiner

FIG 3: management system

CUSHION FOR AN AIRCRAFT SEAT, HAVING INTEGRATED SENSOR ELECTRONICS

CROSS-REFERENCE TO RELATED APPLICATIONS

This application is the United States national phase of International Application No. PCT/EP2020/057793 filed Mar. 20, 2020, and claims priority to German Patent Application No. 10 2019 203 979.0 filed Mar. 22, 2019, the disclosures of which are hereby incorporated by reference in their entirety.

BACKGROUND OF THE INVENTION

Field of the Invention

The disclosure relates to a cushion, in particular a seat cushion for an aircraft seat with integrated sensor electronics, an aircraft seat comprising such a cushion, a management system for monitoring parameters of a passenger sitting on the aircraft seat, and a method for monitoring parameters of a passenger sitting on the aircraft seat.

Description of Related Art

Aircraft manufacturers and their suppliers, as well as airlines, are interested in constantly improving passenger safety, comfort and health. For example, aircrafts may be equipped with devices and systems to monitor and control environmental conditions in the aircraft cabin. For example, passengers can automatically adjust certain conditions, such as temperature and air supply, or seat position.

Electronics in aircraft seats are a constant driver in the development of new in-flight innovations, particularly in the form of in-flight entertainment. Electronics have the potential to do much more than inflight entertainment, such as helping passengers avoid complications like thrombosis and other health-related flight issues in addition to predictive maintenance.

However, with the systems currently used in aircrafts, it is only possible to a limited extent to assess the health, safety and comfort of each passenger individually and to warn in good time of potential impairments such as incorrect seating posture or damage to the seat. For example, the comfortable posture assumed by an airplane passenger at the beginning of the flight may change over the course of the flight and lead to discomfort and health problems.

An approach for individual monitoring of safety, comfort and health of aircraft passengers is described in EP 3 141 482 A1. Here, a seat cushion is described in which a sensor is installed that detects mechanical vibrations and electrical noise associated with the passenger. The information recorded by the sensor is matched in a management system and timely indications and warnings are given to the passenger and the aircraft attendants.

The electronics described in EP 3 141 482 A1 are arranged in the form of, for example, a piezoelectric sensor underneath a seat cushion or behind a back cushion. It is also possible to install a sensor in a pillow to monitor the sleeping state of a passenger.

A disadvantage of the approach described in EP 3 141 482 A1, however, is the low measurement sensitivity and accuracy caused by the arrangement of the electronics, e.g. underneath the seat cushion.

This is due, among other things, to the multilayer or multi-layer structure of seat cushions used in aircraft seats. Such seat cushions are made from a pad of plastic or natural materials, although the use of plastic foam is preferred for various reasons. For example, airline seat cushions may be bonded together from a variety of flame retardant open-cell resilient flexible foams of different densities. Instead of adding flame retardants directly into the foam, the seat cushions can also be provided with a flame retardant fabric, as described, for example, in WO 2018/177808 A1.

SUMMARY OF THE INVENTION

The proposed solution is now based on the object of providing a seat cushion for an aircraft seat which enables improved and more sensitive monitoring of the vital parameters of a passenger sitting on the seat cushion, as well as monitoring of the maintenance condition of the seat cushion, compared to known embodiments.

This object is solved according to a first aspect with a cushion having features as described herein.

Accordingly, there is provided a cushion, in particular a seat cushion for an aircraft seat, comprising the following elements:
at least one pad having an upper side and a lower side made of at least one plastic foam;
at least one sensor system, wherein the at least one sensor system is arranged in a region of the pad adjacent to the lower side of the pad;
and
at least one flame protection fabric covering at least one side, preferably the upper side of the at least one pad.

A cushion, in particular a seat cushion or also a back cushion, is thus provided for an aircraft seat in which the sensor electronics are provided in the cushion and are thus integrated into the seat cushion; i.e. the sensor electronics are a component of the seat cushion and can be transported as part of the seat cushion. The sensor system is enclosed by the plastic foam of the cushion. For example, the sensor system may be foamed into the plastic foam, or embedded in the plastic foam, or glued (e.g., between two layers). By being embedded in the pad, the sensor is optimally protected against environmental influences and premature detachment.

In the present case, the upper side of the cushion is to be understood as the side of the cushion facing the passenger, while the lower side of the cushion faces away from the passenger and is thus exposed to the mechanical load of a passenger to a lesser extent than the upper side.

The sensor system is arranged in a lower area of the cushion, in particular in the lower third of the cushion (in relation to the extension between the top and bottom of the cushion), i.e. in the lower area of the cushion facing away from the passenger. This arrangement of the sensor system in the lower area (or also on the underside) of the cushion leads to a longer service life of the sensor system.

In one embodiment, it is provided that more than one sensor system is provided in the cushion. Thus, a second sensor system can be provided in the padding of the cushion, on the padding of the cushion or on the flame protection fabric (possibly covered by a cover). Thus, in addition to the sensor system provided in the lower region of the cushion, at least one second sensor system (e.g., in the form of a sensor foil) may be arranged in the upper region (i.e., in the upper third) of the cushion or also on the upper side of the cushion of the cushion. The use of a second sensor system results in improved measurement accuracy.

As explained further below, it may also be envisaged that further sensor electronics are integrated or incorporated into a cover covering the cushion.

The sensor system used in the cushion of the present cushion preferably includes sensors for pressure measurement, strain measurement, force measurement, and/or deflection measurement.

The pressure sensor provides data for the (dis)use of the cushion. A strain sensor measures the restoring forces of the foam, allowing conclusions to be drawn about the stability and strength of the foam. When pressure is applied to the sensors, an electrical current flow is generated that reflects or reflects the degree and duration of pressure application. The sensor unit is connected to an electronic control unit with receiver and processor unit for receiving and processing the generated current flow.

It should be emphasized that the present sensor system does not mean a heating system; i.e., the use of a heating system is excluded in the present pad.

The sensor system integrated into the cushion (e.g. in the form of printed electronics) enables predictive maintenance and sensor functions, with the information obtained with the sensor system being made available in particular to aircraft manufacturers, seat manufacturers, airlines and maintenance and repair companies, but also to passengers.

The printed pressure sensor array can determine the occupancy of a seat, monitor the condition of the cushion, and also provide parallel suggestions to the passenger to prevent problems such as thrombosis via wireless communication methods. By determining seat occupancy, for example, boarding and weight distribution in the aircraft can be optimized.

As part of predictive maintenance of the cushion (Operators USP), it is possible to determine weights and types of use over the life of the cushion based on the different people using the cushion. This, in turn, allows predictive maintenance to be performed to replace the cushions in a timely manner before the cushions lose passenger comfort due to overuse or vandalism. In addition, a full lifecycle analysis of the cushion is possible, starting with the materials used, through certification and usage, and finally information for seat recycling or resale to low-cost aircraft carriers. The implemented data storage allows the product to be identified during its entire life cycle and is also tamper-proof.

Furthermore, the sensor system integrated into the cushion can offer ergonomic benefits for the passenger (Passenger USP). For example, the sensor system of the cushion can be connected to the passenger via a mobile app. The mobile app reads the data from the sensor system (pressure sensor array; strain sensor array) in the cushion and can provide recommendations to the passenger for an optimal healthy fit. The pressure sensor array of the sensor system also provides information about the pressure distribution and uses it to determine the passenger's seating behavior. This can promote healthy seating behavior, and prevent or reduce chronic diseases caused by poor seating behavior such as thrombosis. In addition, the pressure sensing system of the sensor system can be used to detect the stress level of passengers based on their movements.

The cushion at hand can therefore provide the customer (such as aircraft manufacturer, seat manufacturer, airlines and maintenance companies, passenger) with information on the condition of the cushion as well as the passenger. With regard to service, it is possible to determine, among other things, how much stress the cushion has been subjected to during its service life and how this has affected the hardness and dimensions of the cushion, and whether the cushion needs to be replaced at the next check in the hangar or, in the event of serious faults, between a take-off or landing (e.g. at the gate of an aircraft) or whether it can still continue to fly. The electronics built into the cushion independently reports to the service personnel, knows their number and provides all the necessary information to be ordered. With regard to the passenger, the passenger's sitting behavior can be recorded and, if desired, ergonomic tips can be transmitted to the passenger via a mobile app on how to sit more healthily or actively, for example. Games can also be offered on the board entertainment system in which the game figure can be controlled by shifting the seat, e.g. skiing, racing, balance or skill games, etc.

In one embodiment of the present cushion, the at least one sensor system comprises a flexible substrate having at least one sensor (printed) disposed on the flexible substrate.

The sensor system in the form of printed electronics can include various sensors, such as RFID sensors, contact-free sensors, piezoelectronic sensors. Also, the sensors may be in the form of sensing wires or knitted, crocheted or woven threads arranged in a meandering pattern or each horizontally and vertically with respect to each other. Furthermore, the sensor system may include antennas.

In one embodiment, an RFID tag is provided in the form of an integrated RFID tag suitable for applications on non-metallic surfaces. This RFID tag enables maximum read range for use with handheld mobile scanners, as well as NFC (near field communication), Bluetooth, Ultra-Low-Power Bluetooth, Comprehensive Bluetooth, Cypress Low-Power Bluetooth MCU for Mesh Networking, Bluetooth 5.2. (in the case of 5G bandwidth) or WLAN. For Bluetooth 5.0 ICs, the long range communication feature is recommended to reduce the number of readers needed (LE coded support (125 kbps)). Bluetooth 5.1 can be used because it offers precise location/direction detection as an additional function. In case of RF communication, several readers would have to be installed in the plane due to possible signal interference and short communication range (~7-10 m).

A material or material layer made of polyethylene terephthalate (PET), polyimide (PI) or thermoplastic polyurethane (TPU) is preferably used as the flexible substrate on which the sensors are arranged. The material used for the sensor system is designed to be flame-resistant.

The use of piezoresistive, polymer-based sensors that exhibit high sensitivity is particularly preferred. The carrier material is based on epoxy resins. The application can be as a single sensor or as an RFID sensor unit.

As mentioned above, the sensor system is preferably in the form of printed electronics. In the case of a printed capacitive sensor, the capacitance between two printed electrode plates (respectively located at the bottom and top of the cushion foam) is determined to decrease when the cushion is used due to compression of the foam. A printed resistance sensor measures the decrease in resistance of the sensor electrodes when the cushion is used due to compression of the sensor ink. A printed strain sensor determines the change in resistance of a printed strain gauge (which is preferably foamed in, sandwiched between foam layers, or adhered to the foam) when the cushion is used due to mechanical deformation of the strain gauge.

Silver-containing inks or carbon-containing inks can be used as printing inks. In one embodiment, a sensor system printed on a polymer material (e.g., PET or TPU) using silver ink is used. The printed sensors may have different shapes and sizes. Also, the sensitivity of the sensors can be adjusted by the type, amount and thickness of ink, variations in electrode configuration.

In a particularly preferred embodiment, a printed resistance sensor (FSR) is used. Such a sensor comprises a printed electrode with a printed layer of a pressure-sensitive material (e.g. ink). In one embodiment, the FSR sensor comprises a silver electrode printed on a PET film or TPU film with insulator material and pressure sensitive material (printed FSR sensor ink) disposed thereon, such that when pressure is applied to the sensor, a switch is closed and the reduced resistance is measured (e.g., by an MCU connected to the sensor). Based on the resistance of the closed switch, the acting force, pressure or weight can be determined.

An energy storage device (battery/supercap) can be used to ensure a reliable power supply. A battery-powered solution is the most cost-effective and time-efficient here.

As mentioned above, the sensor system is enclosed by the plastic foam of the cushion or is embedded in the plastic foam. Thus, the sensor system can be inserted, e.g. foamed, into the pad (or other structure) during production. Integral insertion between laminate layers or foam layers is also possible. This is possible due to the chemical compatibility of the sensor with the material of the padding (or other structure), whereby an optimal chemical bond can be created.

The cushion used in the present cushion is made of a plastic foam, preferably polyurethane foam, polyurethane-graphite foam, polyethylene foam, polystyrene foam, polycarbonate foam, polyether foam, polyester foam, PVC foam, silicone foam, or PMMA (polymethyl methacrylate) foam. Preference is given to the use of a cushion made of an (open-cell) polyurethane foam. It is also possible for further fiber materials, in particular high-temperature-resistant fibers, to be embedded in the plastic foam.

Polyurethane foams are typically prepared from an isocyanate or a mixture of at least two isocyanates, such as toluene-2,4-diisocyanate (TDI) or diphenylmethane diisocyanate (MDI), optionally used as prepolymer, and a polyol or a mixture of several polyols, for example a polyether polyol or a polyester polyol, and water as base components. The at least one isocyanate and the at least one polyol are preferably added in such a proportion that a ratio of the functional groups —NCO/—OH is set in a range between 0.20:1, in particular 0.85:1 and 0.95:1, in particular 1.2:1.

Further additives, such as a catalyst or activator, defoamers, colorants can be added. Color pigments, such as titanium oxides, in particular titanium dioxide, barium sulfate, ion exchangers, polyethylene, polypropylene, polyester, activated carbon, polymer superabsorbers for absorbing moisture and flame retardants can be used as additives.

In general, it should be noted that the foams used must meet the specific requirements in the aircraft industry. A simple transfer of properties from one foam to another is not possible in the aircraft industry. In particular, the strict requirements for the fire behavior of foams in the aircraft industry must be met.

The cushion may comprise one or more foam layers or foam sheets. In the case of a multilayer pad, the different foam layers may have different strengths or stiffnesses that are adjustable during foam production.

As already indicated above, the at least one sensor system can be inserted or arranged between these foam layers. In the case of two sensor systems, for example, the following layer structures of the pad can be provided (viewed from bottom to top): first foam layer-first sensor system-second foam layer-opt. third foam layer-second sensor system-opt. flame protection fabric. Overall, various arrangements are conceivable, which are described in more detail below.

As indicated above, it would also be possible to attach the sensor system to the underside of the pad (e.g. by means of a non-detachable connection). A non-detachable connection can be made, for example, by gluing or sticking the sensor system to or onto the pad using suitable adhesives. Suitable adhesives may be flame retardant adhesives, such as thermoplastic co-polyamide adhesives or water-based adhesives. Particularly preferred are moisture-reactive hot melt adhesives based on polyurethane prepolymers that react with ambient moisture to form high molecular weight polymers.

In a further embodiment of the present cushion, the sensors of the at least one sensor system are arranged in the cushion in the buttocks area and/or along the thighs of a seated passenger. This arrangement of the sensors enables specific monitoring of the regions or areas in the cushion that are subjected to the greatest stress during the passenger's sitting process. As mentioned above, two sensor systems can also be used for this purpose, with a first sensor system being arranged in the lower third of the cushion and a second sensor system being arranged in the upper third of the cushion of the cushion.

As noted, the at least one pad with the sensor system is covered by at least one flame protection fabric made of a nonwoven or woven fabric. The flame protection fabric can be provided on one side of the pad, i.e. on the upper side or the lower side, as well as cover the entire pad (i.e. all around from all sides).

The abrasion resistant flame retardant fabric used herein comprises at least one barrier layer of at least one nonwoven fabric of at least one type of flame resistant fiber, and at least one abrasion resistant layer (abrasion layer) provided on the barrier layer of at least one textile fabric with high abrasion resistance of at least one type of fiber, preferably at least two types of fiber.

The at least one abrasion layer used in the present flame protection fabric has an abrasion resistance of at least 30,000 cycles, preferably of at least 45,000 cycles, in particular of at least 55,000 cycles, very particularly preferably of at least 150,000 cycles. The abrasion resistance is determined according to Martinedale DIN ISO 12947 1; BS 5960; 1988. In the test procedure according to Martindale, cotton is used as the standard material. The required level of abrasion resistance of the flame retardant fabric is influenced by the intended use. For example, the abrasion resistance depends on the aircraft structure, e.g. seat bottom shell or fabric (diaframe) or backrest structure, in or on which the flame retardant fabric is used. The aim is to provide a flame protection fabric that can be used for all aircraft structures.

The high abrasion resistance of the textile fabric used for the abrasion layer is due in particular to a large tight mesh and small fiber spacing of the fibers used in the textile fabric. Accordingly, the tensile strength of the textile fabric used for the abrasion layer is in a range between 700 and 1200 N/25 mm, preferably between 800 and 1100 N/25 mm, in particular preferably between 850 and 1000 N/25 mm in the longitudinal direction and in a range between 400 and 800 N/25 mm, preferably between 500 and 700 N/25 mm, in particular preferably between 500 and 600 N/25 mm in the transverse direction. The tensile strength is determined according to DIN 53357-A using a 25 mm wide strip.

The textile material used as the abrasion layer can be a woven, a knitted or a warp-knitted fabric. It is preferred if the textile fabric used has the same appearance on the front and the reverse side.

In the present context, a woven fabric is understood to be a flat textile fabric consisting of at least two thread systems crossed at right angles or almost at right angles, the threads running in the longitudinal direction being referred to as warp threads and the threads running in the transverse direction being referred to as weft threads. The yarns pass over and under the transverse yarns in a certain rhythm (weave). In the fabric used as an abrasion layer, one fiber in the warp direction and one fiber in the weft direction are adjacent to each other. This results in a high degree of tightness, A knitted fabric and a crocheted fabric, on the other hand, are knitted fabrics and are made from thread systems by forming stitches, whereby one loop of thread is looped into another loop of thread. In the case of a crocheted fabric, one loop is made next to the other, i.e. the yarn runs horizontally; while in the case of a knitted fabric, the yarn forms superimposed loops, i.e. the yarn runs vertically. Here, too, a small distance between the fibers results in a high degree of tightness.

In one embodiment, the type of fiber used in the abrasion layer may comprise synthetic or natural fibers.

Polymer fibers selected from the group of polyacrylonitrile fibers (PAN fibers), preoxidized PAN fibers, polyaramide fibers, such as para-aramid fibers (Kevlar) or meta-aramid fibers (Nomex), kynol novoloid or carbon fibers can be used as synthetic fibers. Flame retardant equipped fibers can also be used. Preferred fibers are para-aramid fibers (or alternatively meta-aramid fibers) and polyacrylonitrile fibers (PAN fiber). Flame retardant seed fibers such as cotton fibers or flame retardant bast fibers such as hemp fibers can be used as natural fibers.

In a further embodiment of the present flame retardant fabric, the abrasion layer may also comprise more than one type of fiber. Preferably, two, three or four different fiber types are used, whereby fiber type and fiber proportions can be combined and varied as desired. In a preferred embodiment, only two fiber types are used, with poly-aramid fibers and polyacrylonitrile (PAN) fibers being preferred.

Thus, in the case of the use of two types of fibers in the abrasion layer, the quantitative proportions in each case can vary arbitrarily in a range between 5 and 95 wt %, preferably between 10 and 90 wt %, particularly preferably between 20 and 80 wt %.

In one variant, the abrasion layer can comprise
50 to 90% by weight, preferably 60 to 80% by weight, particularly preferably 70% by weight of a first type of fiber, and
10 to 50% by weight, preferably 20 to 40% by weight, particularly preferably 30% by weight of a second type of fiber.

In a particularly preferred embodiment of the present flame retardant fabric, the at least one abrasion layer consists of
50 to 90 wt %, preferably 60 to 80 wt %, more preferably 70 wt % polyacrylonitrile (PAN) fibers, and
10 to 50 wt %, preferably 20 to 40 wt %, more preferably 30 wt % para-aramid fibers.

In another preferred embodiment of the present flame retardant fabric, the at least one abrasion layer has a basis weight between 100 and 180 g/m², preferably between 110 and 150 g/m2, more preferably between 130 and 140 g/m².

In general, it is conceivable and possible to use more than one textile layer as an abrasion layer, e.g. two, three or four.

The thickness of the abrasion layer is in a range between 0.2 and 1 mm, preferably 0.4 to 0.8 mm, in particular 0.5 mm.

As mentioned above, the abrasion layer may comprise or consist of a fiber blend of fibers based on, for example, polyaramides (especially para-aramid) and polyacrylonitrile.

Polyaramides (aromatic polyamides) are polyamides in which the amide groups are attached to aromatic groups. Aramides belong to the liquid crystal polymers (LCP). The most important types are poly(p-phenylene terephthalamide) (PPTA, trade names: Kevlar, Twaron) and poly(m-phenylene isophthalamide) (PMPI, trade names: Nomex, Teijinconex).

Polyacrylonitrile fibers (PAN fibers) typically consist of 100% polyacrylonitrile. PAN fibers are hard, stiff, resistant to chemicals and solvents, and have a melting point above the decomposition temperature. Copolymer fibers can also be used, which consist of polyacrylonitrile (proportion >85%) and polymethyl methacrylate.

The at least one abrasion layer is preferably applied continuously over the entire surface of the at least one barrier layer as part of the flame retardant fabric, and is thus preferably not in the form of a grid or scrim.

As noted above, the at least one barrier layer comprises at least one nonwoven fabric of at least one type of flame-resistant fiber.

Nonwovens (or nonwovens) are structures made of fibers of limited length, continuous fibers (filaments) or chopped yarns of any kind and origin, which have been joined together in some way to form a nonwoven (a fiber layer, a fiber pile) and bonded together in some way, excluding interlacing or entangling of yarns, as occurs in weaving, knitting (see above). Nonwovens are for the most part flexible textile fabrics, i.e. they are easily bendable, their main structural elements are textile fibers and they have a comparatively small thickness compared to their length and width.

In the present case, the fibers of the nonwoven used as a barrier layer are needled and then smoothed, or calendered (or pressed or ironed between two rollers).

In one embodiment, the type of fiber used in the barrier layer may comprise synthetic or natural fibers. Preferably, the barrier layer comprises synthetic fibers in the form of polymer fibers selected from the group of polyacrylonitrile fibers (PAN fiber), preoxidized PAN fibers, acrylonitrile fibers (e.g. Pyrotex), polyaramide fibers, kynol novoloid, para-aramide (Kevlar), meta-aramide (Nomex), basalt fiber, polysilicic acid (SIALOXOL compounds), carbon fiber are used.

In a further embodiment of the present flame retardant fabric, the barrier layer may also comprise more than one type of fiber. Preferred are two, three or four different fiber types, whereby fiber type and fiber proportions can be combined and varied as desired.

Thus, in the case of the use of two types of fibers in the barrier layer, the quantitative proportions can each vary arbitrarily in a range between 5 and 95% by weight, preferably between 10 and 90% by weight, particularly preferably between 20 and 80% by weight.

In the case of using three types of fibers, the quantitative proportions can be as follows:
50 to 90 wt %, preferably 60 to 80 wt %, more preferably 70 wt % of a first type of fiber,
5 to 30% by weight, preferably 10 to 20% by weight, more preferably 15% by weight of a second type of fiber, and
5 to 30 wt %, preferably 10 to 20 wt %, more preferably 15 wt % of a third type of fiber.

In a particularly preferred embodiment of the present flame retardant fabric, the at least one barrier layer consists of

- 50 to 90 wt %, preferably 60 to 80 wt %, more preferably 70 wt % acrylonitrile fibers (such as Pyrotex fiber),
- 5 to 30% by weight, preferably 10 to 20% by weight, more preferably 15% by weight para-amide fibers, and
- 5 to 30 wt %, preferably 10 to 20 wt %, more preferably 15 wt % pre-oxidized polyacrylonitrile (preox PAN) fibers.

In another preferred embodiment of the present flame retardant fabric, the at least one barrier layer has a basis weight between 50 and 150 g/m$^2$, preferably between 60 and 120 g/m$^2$, more preferably between 70 and 100 g/m$^2$.

The thickness of the barrier layer is between 0.7 and 1.3 mm, preferably between 0.9 and 1.2 mm, more preferably between 1.0 and 1.2 mm.

Also in the case of the barrier layer, it is generally conceivable and possible to use more than one nonwoven layer as a barrier layer, e.g. two, three or four.

As mentioned above, the barrier layer may consist of a fiber blend of acrylonitrile-based fibers (such as Pyrotex), pre-oxidized polyacrylonitrile fibers, and para-aramid fibers.

Pyrotex fibers are flame resistant fibers based on acrylonitrile. Pyrotex fibers are characterized by high acid/base resistance; UV resistance, solvent, hydrolysis and oxidation resistance and continuous temperature resistance up to max. 250° C.

Pre-oxidized polyacrylonitrile fibers (preox PAN fiber) are oxidized PAN fibers with a very high flame resistance.

The present flame retardant fabric is free from fillers, such as inorganic fillers, or other additives. In addition, it has no silicone coating or similar, as often used in the past.

In another preferred embodiment, the present flame retardant fabric comprises at least one intumescent layer. In the context of the solution, the term intumescence refers to an expansion or swelling, i.e., an increase in volume, of a solid body or material. Intumescent materials increase in volume and correspondingly decrease in density when exposed to heat.

In the case of the present flame retardant fabric, the at least one intumescent layer consists of expanded graphite, carbon or suitable flame retardant fibers.

The use of exfoliated graphite as an intumescent layer is particularly preferred. Expanded graphite, also known as expandable graphite, is produced from the naturally occurring mineral graphite. A graphite flake consists of layers of carbon atoms arranged in a honeycomb pattern. Within the layers, the atoms are very tightly bonded by covalent bonds. Only weak bonding forces prevail between the layers, so that molecules can be intercalated between the graphite layers. The intercalation of acids, usually sulfuric acid, converts graphite into exfoliated graphite. When exfoliated graphite is heated, the graphite flakes expand to many times their original volume, depending on the quality, starting at a temperature of approx. 140° C., and presently at approx. 180° C. The evaporation of the incorporated compounds causes the graphite layers to expand in an accordion-like manner. The expanded flakes have a "worm-like" appearance and are usually several millimeters long. One of the main applications of exfoliated graphite is flame retardancy. When exposed to heat, the exfoliated graphite expands and forms an intumescent layer on the surface of the material. This slows down fire spread and counteracts the most dangerous fire consequences for humans, namely the formation of toxic gases and smoke.

The at least one intumescent layer is preferably provided on between the abrasion layer and the barrier layer as an intermediate layer.

In the case of using exfoliated graphite as an intumescent layer, the exfoliated graphite is first introduced into a suitable binder. The abrasion layer is then coated with this solution or suspension.

The at least one exfoliated graphite layer has a basis weight between 30 and 110 g/m$^2$, preferably between 40 and 100 g/m$^2$, more preferably between 50 and 80 g/m$^2$.

The thickness of the exfoliated graphite layer is between 0.1 and 0.3 mm, preferably between 0.1 and 0.2 mm.

In a particularly preferred embodiment, the present flame retardant fabric comprises at least one abrasion layer in the form of a knitted fabric or woven fabric having more than 30,000 cycles of abrasion resistance, at least one intumescent layer in the form of expanded graphite, carbon or various flame retardant fibers, and at least one barrier layer in the form of a needle flow of flame resistant materials.

The layer structure of the present flame retardant fabric is in a preferred variant (seen from top to bottom): abrasion layer-intumescent layer-barrier layer.

The total thickness of the flame protection fabric used in the present case is in a range between 1.5 and 2.5 mm, preferably between 1.8 and 2.0 mm, with a total weight between 200 and 300 g, preferably between 220 and 280 g, more preferably between 250 and 270 g.

In a further variant, the layer structure comprising abrasion layer, optionally intumescent layer and barrier layer is laminated, concealed, bonded or needled.

In a preferred embodiment of the present cushion, at least one foam part or foam layer is provided between the at least one sensor system and the at least one flame protection fabric. The additional foam layer serves in particular to prevent the passenger from feeling the sensor system in the cushion in an uncomfortable manner.

The additional foam layer preferably consists of polyurethane foam, polyethylene foam, polyether foam, polyester foam, silicone foam or may also comprise a plastic fabric, preferably of polypropylene, polyethylene, polyacrylate. It is also possible to foam expanded graphite into the foam layer.

The at least one flame retardant fabric is bonded to the at least one foam member.

Also, in one embodiment, at least one cover may be provided on the top surface of the flame retardant fabric. The at least one cover may be laminated, concealed, bonded or sewn to the at least one flame protection fabric. This cover may be made of leather, artificial leather or a (haptically pleasant) decorative fabric.

In a preferred embodiment, a cover (for the cushion or for the backrest) made of functional textiles (such as. Goretex) is used. Such functional textiles are nowadays used in all walks of life, especially in sports. Depending on their use, these functional textiles are windproof, waterproof, breathable, thermoregulating, dirt-repellent, antimicrobial, flame-retardant, UV-resistant, electrically shielding, elastic, hard-wearing, easy-care, chemical-resistant, lightweight, warming/cooling. In particular, a cover made of functional textiles prevents the passengers from sweating back and from heat accumulation. Due to the breathable textiles, the sweat is transported away from the passenger.

The mentioned materials of the cover for cushion or backrest are preferably laminated on a thin foam. The thickness of the cover fabric can be between 5 and 15 mm, preferably 10 mm.

According to the proposed solution, a sensor system is also provided in the cover (for seat cushion and/or backrest). The sensor system built into the cover is preferably used to measure pressure, temperature and humidity. The use of a temperature sensor in the cover makes it possible to provide information regarding the temperature development in the seat and/or backrest and thus also regarding the condition of the air conditioning system. A moisture sensor in the cover can determine, for example, contamination of the cushion by liquids.

As a sensor system in the cover, threads of conductive materials are used in particular, which are incorporated into the crocheted fabric, knitted fabric, woven fabric, or are laminated between the leather/artificial leather material and foam. Since artificial leather consists of several layers, the conductive materials can also be incorporated directly into the artificial leather.

The cover can be provided in different variants in connection with the cushion:
Textile/leather/imitation leather with integrated sensors-foam layer-cushion with or without integrated sensor system(s),
Textile/leather/imitation leather with integrated sensors-no foam layer-cushion with or without integrated sensor system(s)

The sensor system or sensor array built into the cover can detect different sitting positions (e.g. 5 different sitting positions) and sitting postures. It allows time recording of sitting duration, comparing sitting behavior with health guidelines, intervening and encouraging to change sitting posture. The flight crew can detect the status of the seat temperature in case of overheating or hypothermia and thus pro-actively assist passengers with a wool blanket or adjust the ceiling fan in case of back sweat or freezing.

This results in various design variants for the present cushion with the following layered structure (from bottom to top):
a) Padding with at least one sensor system;
b) Padding with at least one sensor system-flame protection fabric;
c) Padding with at least one sensor system-flame protection fabric-cover without sensor system;
d) Padding with at least one sensor system-flame protection fabric-cover with sensor system,
e) Pad with two sensor systems-flame protection fabric;
f) Pad with two sensor systems-flame protection fabric-cover without sensor system;
g) Pad with two sensor systems-flame protection fabric-cover with sensor system.

These variants can also be provided in a back cushion.

As stated above, the present cushion is preferably used for aircraft seats for determining seat occupancy, monitoring the degree of wear and predictive maintenance, and passenger seating behavior in combination with a computer-implemented method.

For this purpose, a management system is provided which comprises
at least one sensor unit in any of the previously described cushions and/or cover;
at least one processing unit (PU) for processing the data measured by the sensor unit;
at least one storage unit (SU) for storing the measured and processed data, and
at least one display unit for displaying the processed data.

The at least one display unit may be provided on a mobile device such as a smartphone, tablet or on stationary e.g. in the backrest of an aircraft seat. Thus, the sensor system of the cushion may be connected to the passenger via a mobile app on the smartphone. The mobile app reads the data from the pressure array in the seat shell and can provide the passenger with recommendations for an optimal healthy seat.

The data measured and processed by the sensor unit is transmitted wirelessly, e.g. via Bluetooth (or other systems, see above), to the at least one display.

The processing unit can also be connected to the aircraft's network system via a network interface, and thus access possible databases in which, for example, passenger health data is stored. This can be a server on board or in a cloud system (AWS-Amazon Web service, Microsoft Azure, Google, Crossplatforms, Docker cloud hosting (Airbus Skywise) or other adequate systems of other aircraft manufacturers.

It is also conceivable that the present management system has a management module with individual passenger health, safety and comfort data.

In one embodiment, the present management system comprises the following components: sensors (e.g. 8 sensors) as sensor unit; control unit; processing and storage unit; tablet or smartphone as display. The sensors are operated autonomously via Bluetooth in connection with the tablet (or smartphone) accordingly and enable contact with the manufacturer of the software and control of the sensors.

The management system described enables the implementation of a computer-implemented process for determining seat occupancy, monitoring the degree of wear and tear, and predictive maintenance, as well as passenger seating behavior.

The computer-implemented process includes:
measuring the change of at least one parameter selected from temperature, pressure and/or strain by the sensor unit arranged in the cushion and/or in the cover, wherein the parameter change is exerted/caused by a passenger sitting on the cushion;
processing the measured data in the at least one processing unit and storing the data in the at least one storage unit of the management system, and
displaying the processed data on the at least one display unit.

The execution of the described computer-implemented method is performed by a suitable computer program. This computer program comprises instructions which, when the program is executed by a computer, cause the computer to execute the (computer-implemented) method.

The computer program is stored in the memory unit of the management system or on a suitable data carrier. The memory unit of the management system and the data carrier are to be understood as a computer-readable storage medium. Preferably, the computer program is part of the platform of the aircraft. The computer program can be applied independently online in connection or offline without connection to the platform in the aircraft.

The data obtained can be displayed to the flight crew in the cabin and/or to the passenger and can be used in various ways.

For example, by determining seat occupancy, boarding and weight distribution in the aircraft can be optimized, resulting in fuel (kerosene) savings.

The data obtained also provides an indication of the length and severity of cushion use. This in turn enables predictive maintenance to be carried out in order to replace the cushion in good time. The present method can also be used to identify the cushion throughout its service life due to the integration of the sensor electronics in the cushion.

Furthermore, the present method makes it possible to provide information to the passenger regarding his or her seating behavior, alerting the passenger to possible consequences of his or her seating behavior. Thus, in case of a strong deviation of the measured data from a standard value, a message can be transmitted to the passenger and/or also to the flight attendants in order to draw attention to possible problems.

The placement of the sensor unit in the cushion also allows studies to be conducted on the pressure distribution in the cushion when used by a passenger (pressure mapping). Thus, the pressure distribution in the cushion can provide information about areas of high pressure and postural abnormalities. Based on this information, stability and seating comfort can be improved, such as using a more stable foam in the back of the knees to improve seating position and reduce weight.

In a second aspect, the problem to be solved by the proposed solution is solved by a cushion having features as described herein.

Accordingly, there is provided a cushion for an aircraft seat comprising the following elements:
at least one pad made of at least one plastic;
at least one stabilizing means embedded in the at least one pad, and
at least one sensor system arranged on the at least one stabilizing means.

The stabilizing means embedded in the cushion pad is more dimensionally stable than the plastic material of the cushion and has a high modulus of elasticity. Accordingly, the stabilizing means imparts increased mechanical stability and strength to the cushion. Another advantage of the embedded stabilizing means is its interchangeability, i.e. in the event of damage to the stabilizing means, for example, there is the possibility of removing the damaged stabilizing means and replacing it with a new part.

The arrangement of a sensor system on the stabilizing means makes it possible to predict possible wear and damage to the stabilizing means in good time. With the sensor electronics used here, load effects on the stabilizer can be made visible and the material condition monitored. In particular, resistance and elongation behavior can be measured.

The sensor system is preferably pressed, laminated or bonded to the material of the stabilizing means (e.g. a composite).

In one embodiment, the at least one stabilizing means comprises spaced-apart profiled support rails or support plates.

The number of support rails used is determined by the width of the cushion. Thus, in one variant, at least 2, preferably 3, support rails can be arranged in the cushion. The support rails have a preferred center-to-center spacing of 100 to 150 mm, in particular 120 mm. The edge-to-edge distance is preferably 50 to 80 mm, preferably 60 to 65 mm. For a cushion width of 450 mm, the minimum distance (center-to-center) is 100 mm.

The support rails can be curved, with a U-profile or a trapezoidal profile being particularly preferred. The wall thickness of the rails is between 0.5 mm and 5 mm, preferably between 1 and 4 mm, in particular preferably between 2 mm and 3 mm. The depth of the U-profile or trapezoidal profile is in a range between 5 and 15 mm, preferably between 10 and 12 mm.

In a particularly preferred embodiment, at least one side end of the support rail profile is provided with a rounding, i.e. a profile nose, to prevent damage to the foam by sharp edges. The profile rounding is preferably provided on the front side of the cushion (i.e. in the back of the knee), but can also be possible on both sides.

The support rails can be made of a light metal, such as aluminum, or also of a suitable plastic material. Fiber materials, such as carbon fibers or glass fibers, have also proved particularly advantageous in this case. The fibers are embedded in a resin system, such as a phenolic resin or epoxy resin. The carrier rails can be profiled, for example, by compression molding of fiber wet laminates or the sheet molding compound (SMC) process.

In a particularly preferred embodiment, the support rails are provided with a flame-retardant material, in particular in the form of a flame-resistant fabric, which is suitably bonded to the support rails.

A suitable fabric includes, for example, high-temperature-resistant fibers made of glass, plastic or graphite. Particularly preferred temperature-stable fibers are plastic fibers based on polypropylene, polyacrylate or polyamides such as aramids or polybenzimidazole. The latter is particularly advantageous if the carrier rail itself is already made of flame-resistant material; otherwise, flame-resistant fabric can also be used).

In a preferred embodiment, the flame-resistant fabric consists of several layers of fire-resistant material and compressed textiles. For example, a first layer may consist of high-temperature stable fibers, a second (middle) layer may consist of a prepreg fabric, and a third layer may again consist of high-temperature stable fibers.

Furthermore, reference is made to the above statements on the structure of the cushion and their use, which also apply here.

It is further preferred if the present cushions are coupled to at least one support element as part of a support frame of an aircraft seat. In particular, it is envisaged that the cushions are attached to the at least one support element by means of a fastening means, in particular in the form of adhesive tapes or loop tapes. It is also conceivable that the fastening means are already incorporated into the stabilizing means (by means of SMC or compression molding).

In one embodiment, the support element of the aircraft seat support frame comprises at least two struts or spars arranged parallel to each other. In the installed state of the cushion and the aircraft seat, the struts of the support element run transversely to the longitudinal direction of the aircraft; i.e. the struts of the support element run parallel to the direction of extension y and therefore parallel to the width b of the cushion.

BRIEF DESCRIPTION OF THE DRAWINGS

The solution is explained in more detail below with reference to the figures in the drawings.

DESCRIPTION OF THE INVENTION

Figure 1:
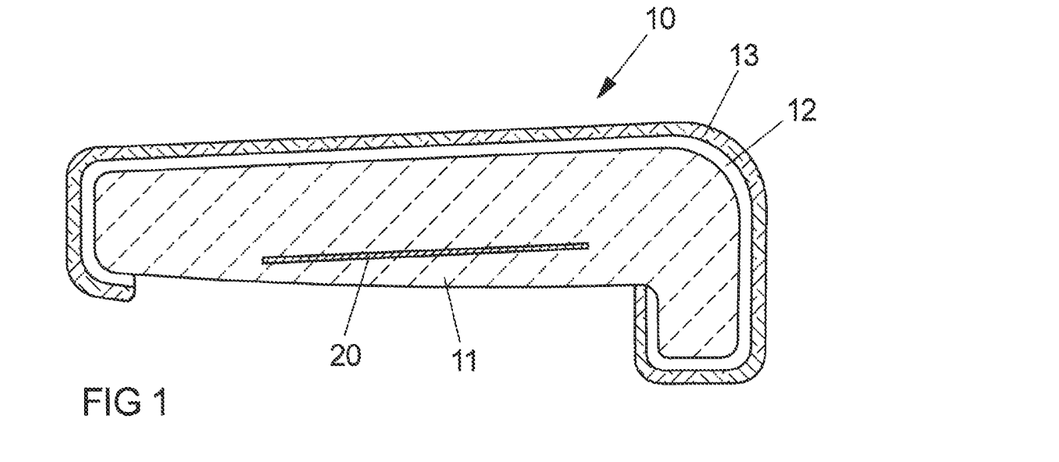
FIG. 1 shows a schematic view of a cushion with integrated electronics according to a first embodiment.

FIG. 1 shows a first embodiment of a cushion 10 with integrated electronics for an aircraft seat. The top seat area of the cushion 11 is completely surrounded by a flame protection fabric 12. A protective cover or covering 13 is attached to the cushion including the flame retardant fabric by means of adhesive or loop tapes. The cover 13 extends over the entire upper side of the pad including the back of the knee area.

A sensor system 20 is provided in the cushion 11. The sensor system 20 arranged in the cushion 11 comprises pressure and strain sensors which are foamed in within the cushion 11 in an area adjacent to the underside of the cushion 11. By placing the sensor system in the lower third of the pad 11, the sensor is optimally protected from environmental influences. It is also possible that a second sensor system is additionally provided in the upper area (in the upper third) of the pad (not shown).

The flame protection fabric 12 consists of a barrier layer and an abrasion layer. The abrasion layer is provided on one side (here on the upper side) of the barrier layer.

The barrier layer consists of a nonwoven made of 70% Pyrotex(bi-grade) fibers (acrylonitrile fibers), 15% para-aramid fibers(regenerated) and 15% preox PAN (polyacrylonitrile) fibers. The basis weight of the barrier layer in this case is 70 g/m². The abrasion layer consists of a fabric made of 70% PAN (polyacrylonitrile) fibers and 30% para-aramid fibers. The basis weight of the abrasion layer is 130 g/m².

In addition to the barrier layer and abrasion layer, a third intumescent layer of exfoliated graphite can be provided in the flame retardant fabric, the exfoliated graphite starting to expand at 180° C. The exfoliated graphite layer is provided as an intermediate layer between the abrasion layer and the barrier layer. The exfoliated graphite layer is applied to the abrasion layer with a basis weight of 50 g/m².

It is also possible that the flame protection fabric and a foam part (or foam layer) made of various foams are glued or laminated together. In this case, the sensor electronics are provided between the pad and the foam layer (not shown).

Figure 2A:
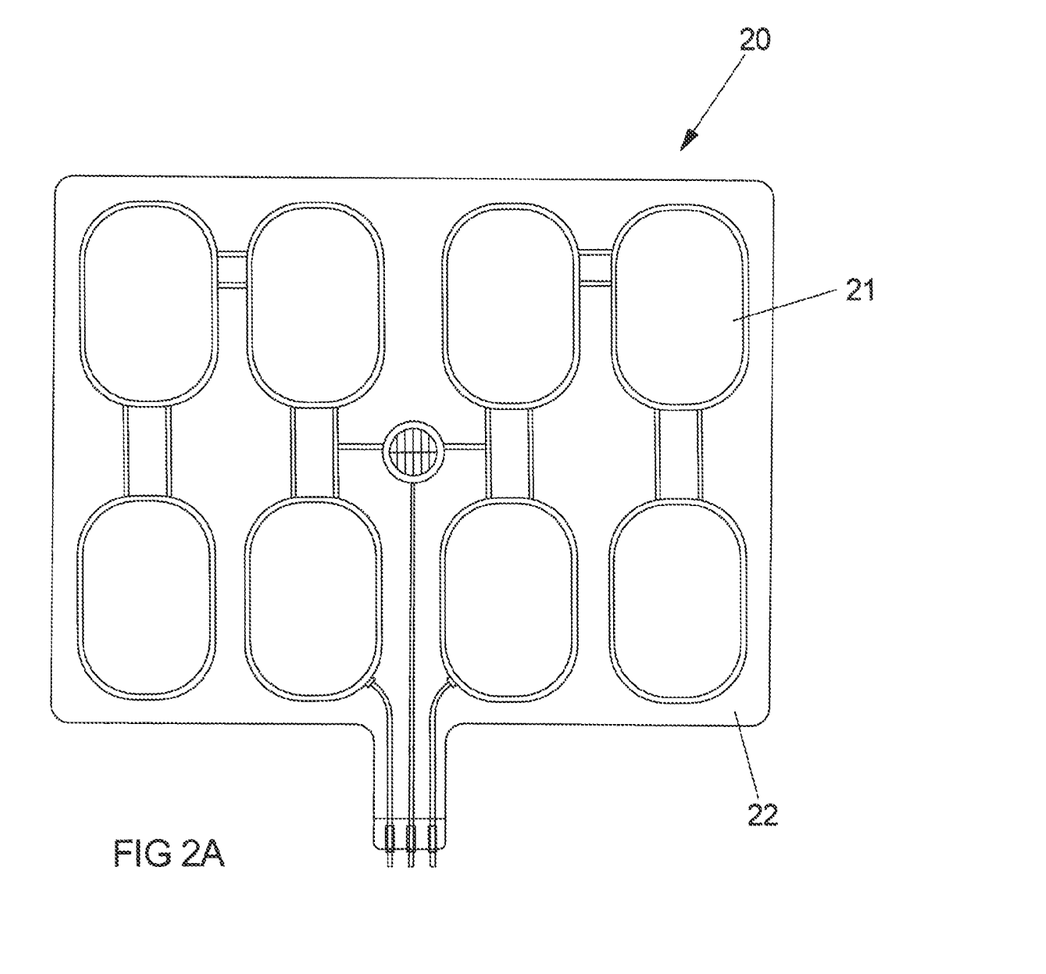
FIG. 2A shows a schematic view of a first sensor system integrated into a cushion.

FIG. 2A shows the structure of a first sensor system 20 integrated in a cushion. This first sensor system (in the form of an RFID sensor unit) comprises eight sensors 21 in the form of polymer strain gauge sensors. The carrier material 22 is epoxy resin-based. The sensor system 20 detects the change in length (strain) during mechanical deformation of a component made of polymer composites. The resistance range and k-factor of the sensor are adjustable. The sensor system 20 is bonded to the pad 11.

Figure 2B:
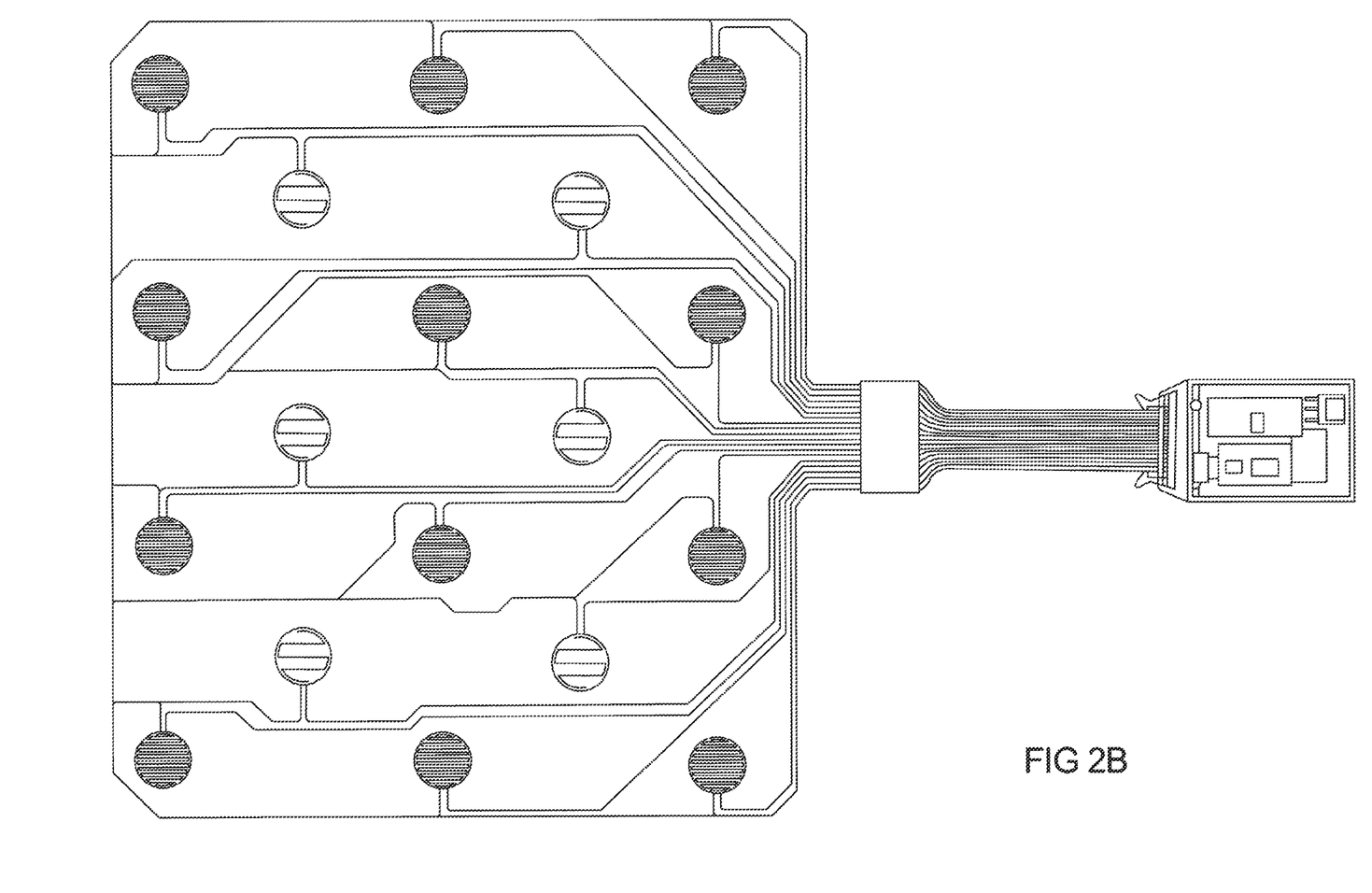
FIG. 2B shows a schematic view of a second sensor system integrated into a cushion.

FIG. 2B shows the structure of a second variant of a sensor system 20, which can be integrated into a cushion.

The sensor system shown in FIG. 2B comprises FSR pressure sensors (12 in total; shown in dark) and other sensors (6 in total). The FSR pressure sensors each comprise a silver electrode printed on a PET film or TPU film with insulator material and pressure sensitive material (printed FSR sensor ink) placed on it, so that when pressure is applied to the sensor, a switch is closed and the reduced resistance is measured (e.g. by an MCU connected to the sensor). The 6 other sensors are e.g. sensors that ensure that the sensor is only active (saving energy consumption) as soon as it is occupied, so that "occupied" or "not occupied" is displayed.

Figure 3:
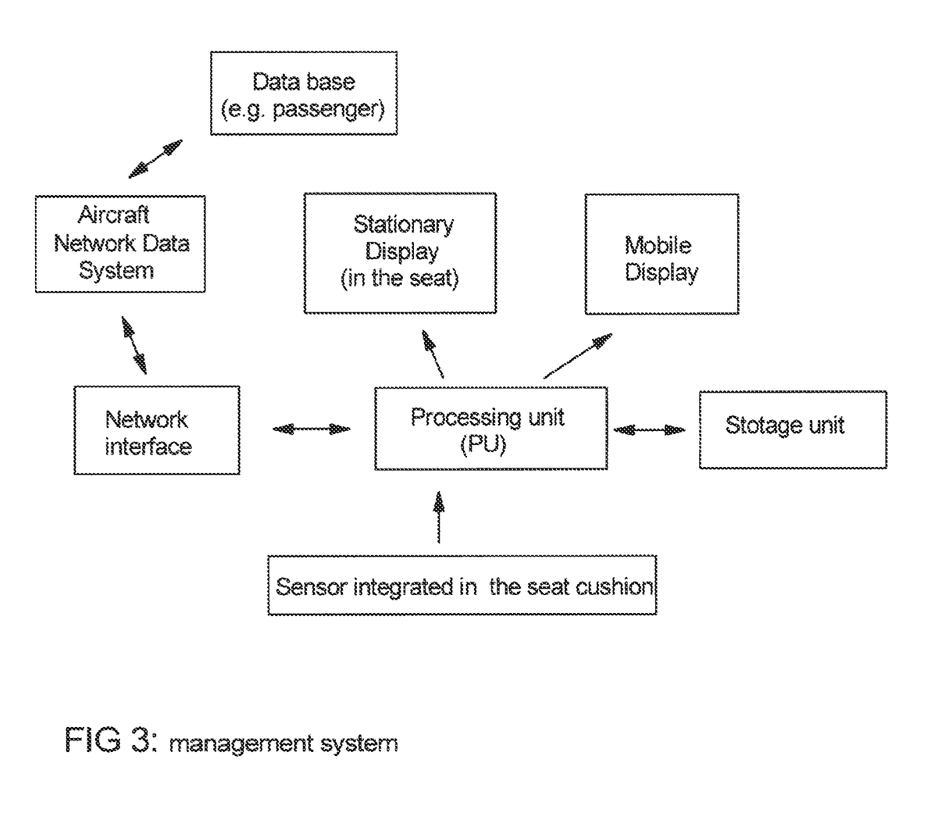
FIG. 3 shows a block diagram of an embodiment of a management system for the use of a sensor system integrated in a cushion.

FIG. 3 shows a block diagram of a management system for using a sensor system integrated into a cushion. The management system comprises a sensor unit integrated into a cushion; a processing unit (PU) for processing the data measured by the sensor unit; a storage unit (SU) for storing the measured and processed data; and a display unit for displaying the processed data.

The display unit can be provided on a mobile device such as a smartphone and/or tablet or on stationary e.g. in the backrest of an aircraft seat. Thus, the sensor system of the cushion may be connected to the passenger via a mobile app on the smartphone and/or tablet. The mobile app reads the data from the pressure array in the seat shell and can provide the passenger with recommendations for an optimal healthy seat.

The data measured and processed by the sensor unit is transmitted wirelessly, e.g. via Bluetooth, to the at least one display.

The processing unit can also be connected to the aircraft's network system via a network interface, and thus access possible databases in which, for example, passenger health data is stored.

Figure 4A:
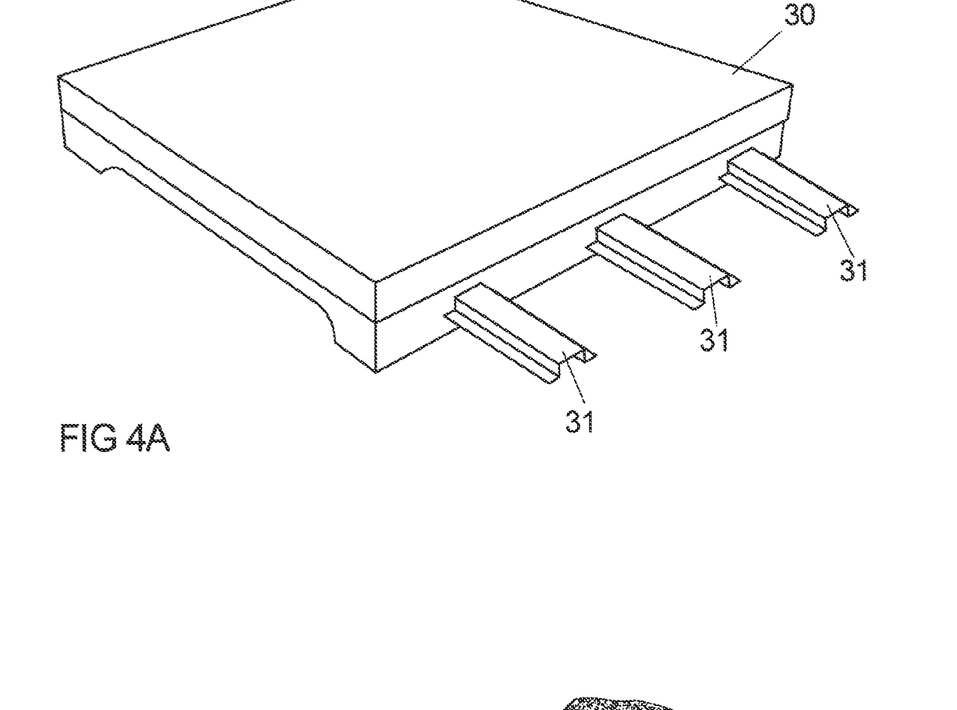
FIG. 4A shows a schematic view of a cushion with integrated electronics according to a second embodiment.

In the embodiment of the cushion with a pad 30 shown in FIG. 4A, a stabilizing means in the form of U-shaped support rails 31 is provided.

The support rails 31 have a U-profile. The wall thickness of the support rails 31 is between 1.5 and 2 mm. The support rails 31 consist of carbon fibers or glass fibers. The fibers are embedded in a resin system, such as a phenolic resin or epoxy resin. The support rails can be profiled, for example, by compression molding of fiber wet laminates or by means of the sheet molded compound (SMC) process.

In the embodiment shown in FIG. 4A, three support rails 31 are shown parallel with a center-to-center spacing of 100 mm in a pad 30 (with a width of 450 mm). The support rails 31 have a U-profile or a trapezoidal profile. The depth of the U-profile or trapezoidal profile is in a range between 10 and 12 mm.

Figure 4B:
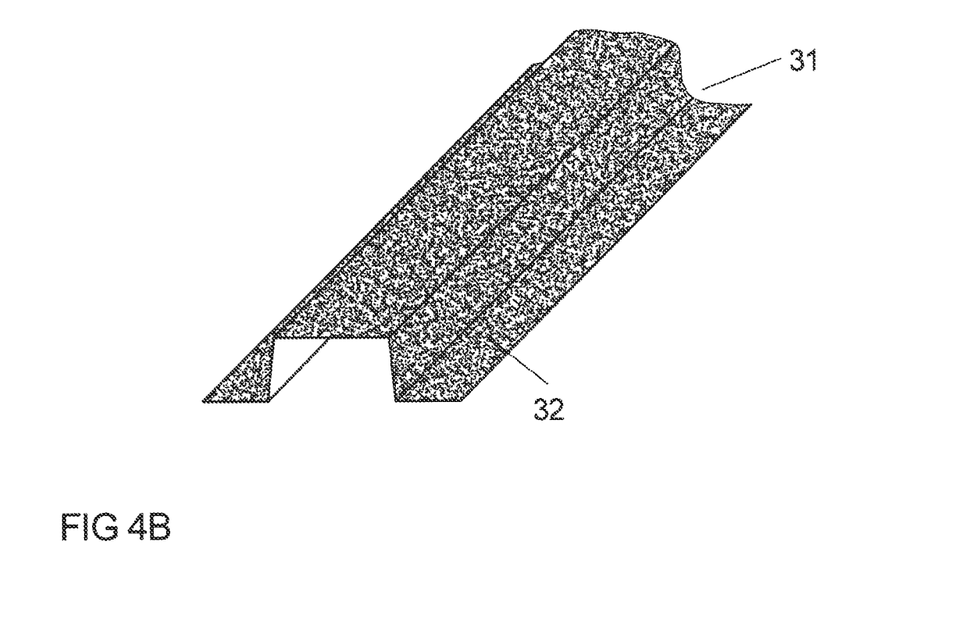
FIG. 4B shows a schematic cross-sectional view of a support rail integrated into a cushion of FIG. 4A.

The support rails 31 are either made of a flame-resistant material or are additionally provided with a flame-retardant material in the form of a flame-resistant fabric 32 made of temperature-stable fibers are plastic fibers based on polypropylene, polyacrylate or polyamides such as aramides or polybenzimidazole. For this purpose, the support rails 31 can be laminated with the flame-resistant fabric 32 (see FIG. 4B).

A sensor system is provided on the support rails. The sensor unit described in FIG. 2 can be pressed, laminated or glued to the material of the support rails.

FIGS. 5A-I show different variants of arrangement and combination of cushion with sensor system and cover.

Figure 5A:
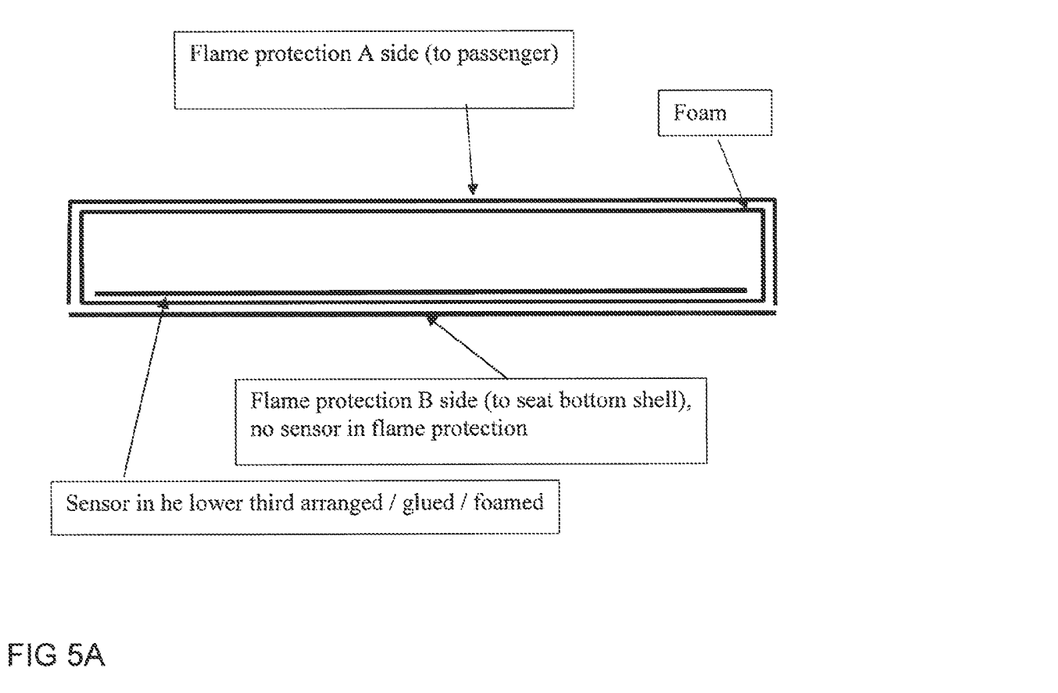
FIG. 5A shows a schematic view of a structure of a cushion with a sensor system.
Figure 5B:
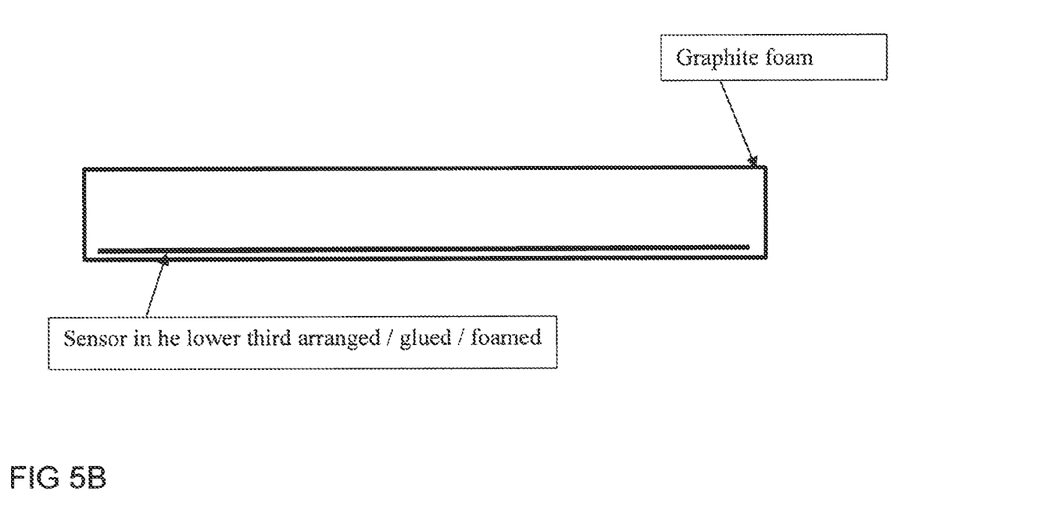
FIG. 5B shows a schematic view of a further structure of a cushion with a sensor system.

FIG. 5A shows a cushion or back cushion in an application with flame protection all around and a sensor provided in the lower third of the cushion. FIG. 5B shows a cushion or back cushion in an application without flame protection and a sensor provided in the lower third of the cushion. In another variant, it is also possible to apply the flame protection only on one side of the cushion, i.e. on the upper side or the lower side (not shown).

Figure 5C:
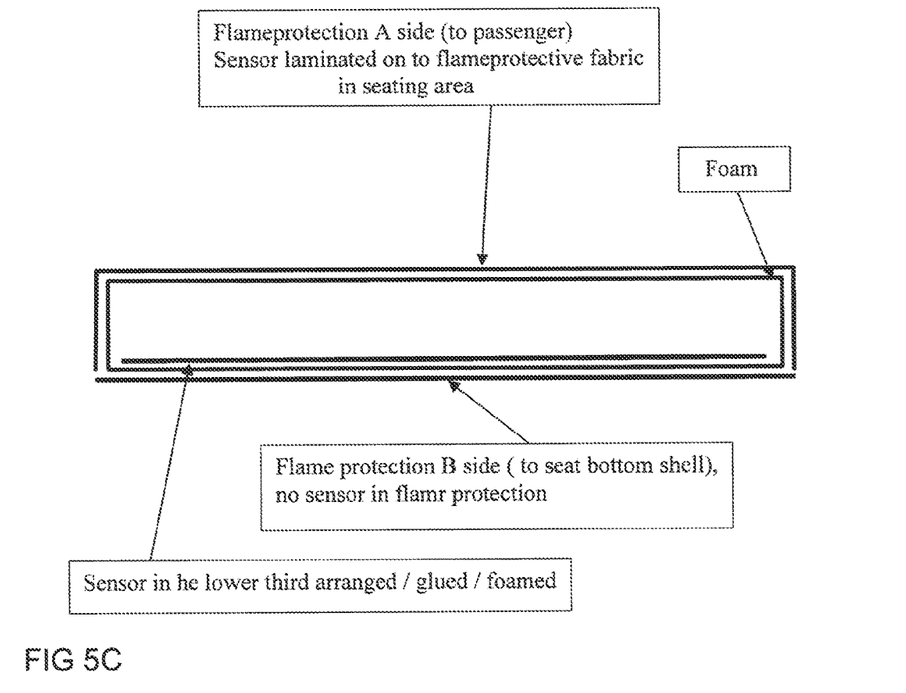
FIG. 5C shows a schematic view of a setup of a cushion with two sensor systems.
Figure 5D:
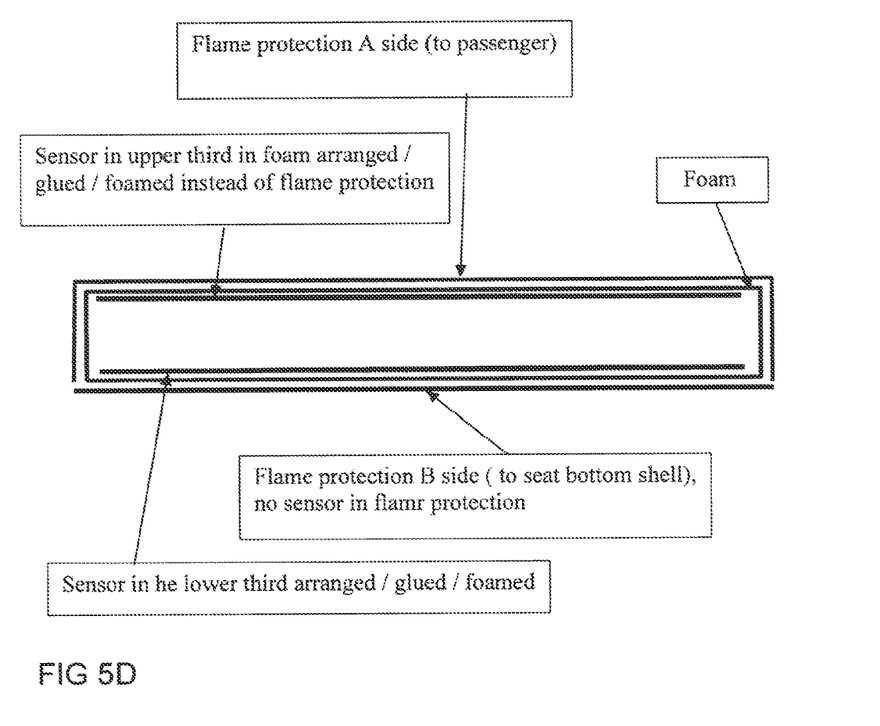
FIG. 5D shows a schematic view of another setup of a cushion with two sensor systems.
Figure 5E:
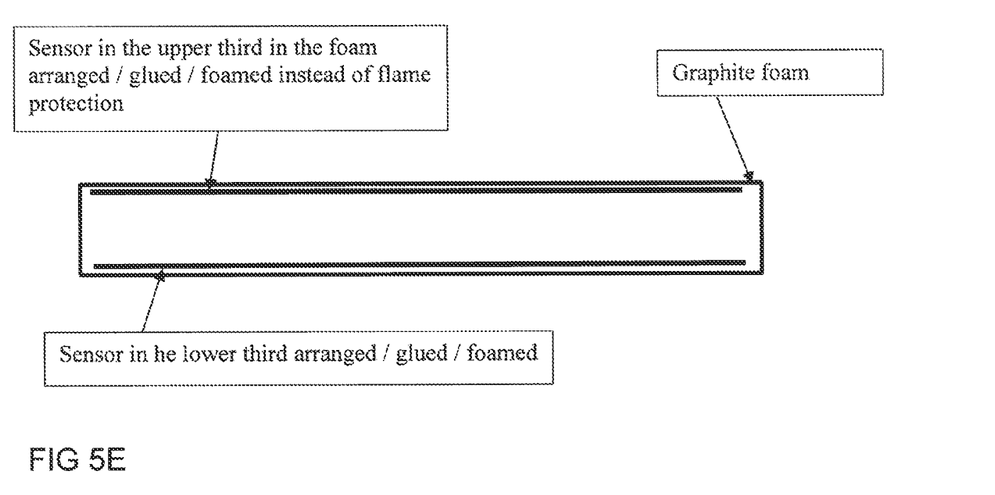
FIG. 5E shows a schematic view of another setup of a cushion with two sensor systems.

FIG. 5C shows a cushion or back cushion for use with flame protection all around and 2 sensors, whereby a first sensor is provided in the lower third of the cushion and a second sensor is laminated onto the flame protection fabric. In the cushion of FIG. 5D, in contrast to the cushion of FIG. 5C, the second sensor is provided in the upper third of the cushion. FIG. 5E shows the cushion of FIG. 5D without flame protection fabric.

Figure 5F:
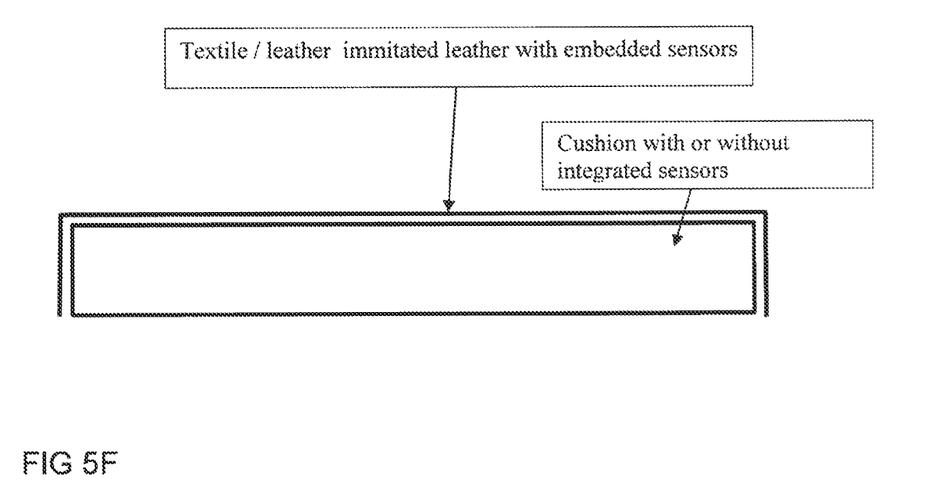
FIG. 5F shows a schematic view of a structure of a cushion with a cover with sensor systems.
Figure 5G:
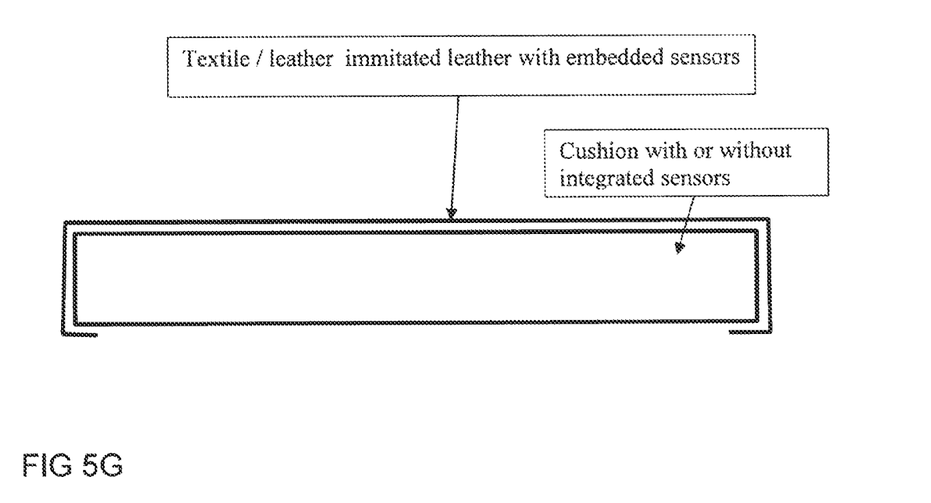
FIG. 5G shows a schematic view of a further structure of a cushion with a cover with sensor systems.
Figure 5H:
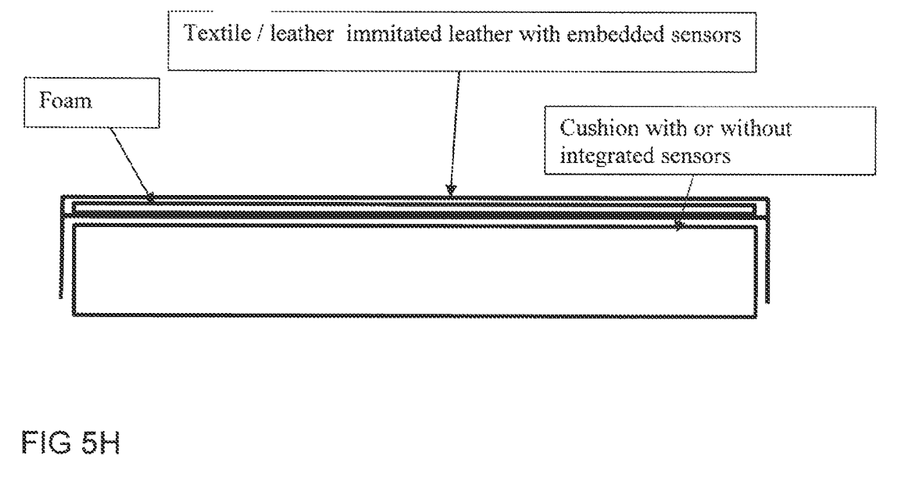
FIG. 5H shows a schematic view of a further structure of a cushion with a cover with sensor systems.
Figure 5I:
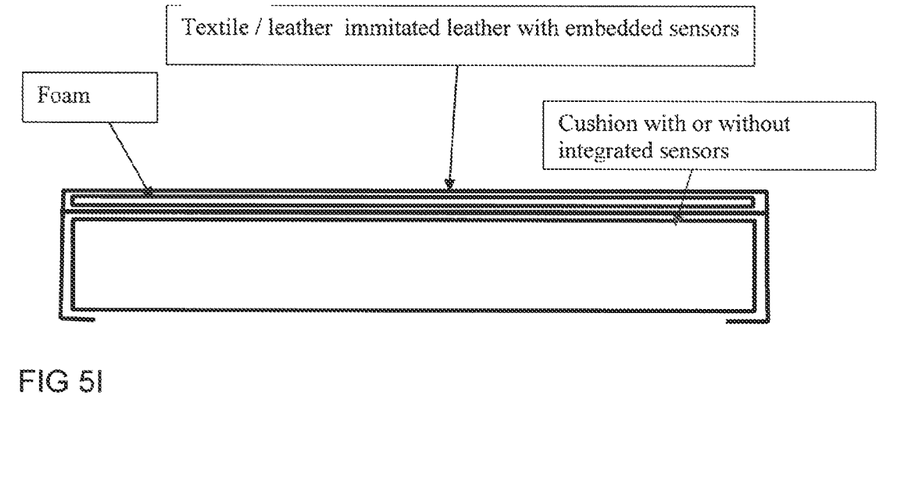
FIG. 5I shows a schematic view of a further structure of a cushion with a cover with sensor systems.

FIG. 5F shows a cushion with a partial cover in which sensors are incorporated, and a foam layer is provided between the cushion (with or without sensors) and the cover. In the variant shown in FIG. 5G, the cover extends to the underside of the cushion, FIG. 5H shows a cushion with a partial cover in which sensors are incorporated and no foam layer is provided between the cushion (with or without sensors) and the cover. In the variant shown in FIG. 5I, the cover extends to the underside of the cushion.

The invention claimed is:

1. A cushion for an aircraft seat, comprising
    at least one pad having an upper side and a lower side made of at least one plastic foam;
    at least one sensor system, the at least one sensor system being arranged in a region of the pad adjacent to the lower side of the pad;
    at least one flame protection fabric covering at least one of the upper side and the lower side of the at least one pad; and
    at least one cover on the side of the at least one pad having the flame protection fabric,
    wherein a further sensor system is provided in the pad, on the pad, or on the flame protection fabric covered by the at least one cover.

2. The cushion according to claim 1, wherein the at least one sensor system comprises sensors for pressure measurement and/or strain measurement.

3. The cushion according to claim 1, wherein the at least one sensor system comprises a flexible substrate having at least one sensor disposed on the flexible substrate.

4. The cushion according to claim 1, wherein the at least one sensor system is enclosed by the plastic foam of the cushion.

5. The cushion according to claim 1, wherein the sensors of the at least one sensor system are arranged in the cushion in the buttocks area and/or along the thighs of a seated passenger.

6. The cushion according to claim 1, wherein at least a second sensor system is provided in the cushion.

7. The cushion of claim 6, wherein the at least one second sensor system is arranged in an area of the cushion adjacent to the upper side of the cushion.

8. The cushion according to claim 1, wherein the cushion consists of several foam layers.

9. The cushion according to claim 8, wherein the at least one sensor system is arranged between two foam layers.

10. The cushion according to claim 1, further comprising at least one flame retardant fabric comprising:
    at least one barrier layer comprising at least one nonwoven fabric of at least one type of flame-resistant fiber, and
    at least one abrasion-resistant layer provided on the barrier layer comprising at least one textile material with high abrasion resistance made of at least one type of fiber.

11. The cushion according to claim 1, wherein the at least one flame retardant fabric comprises at least one intumescent layer.

12. The cushion according to claim 1, wherein the at least one cushion is made of a plastic foam comprising polyurethane foam, polyethylene foam, polyether foam, polyester foam, or silicone foam, or of a plastic fabric comprising polypropylene, polyethylene, or polyacrylate.

13. The cushion according to claim 1, further comprising at least one cover provided at least on the upper side of the flame retardant fabric.

14. An aircraft seat comprising at least one cushion according to claim 1.

15. A management system for monitoring the degree of wear and predictive maintenance as well as the passenger's seating behavior comprising:
    at least one sensor unit in one of the cushions according to claim 1;
    at least one processing unit for processing the data measured by the sensor unit;
    at least one storage unit for storing the measured and processed data, and
    at least one display unit for displaying the processed data.

16. A computer-implemented method for determining seat occupancy, monitoring the degree of wear and predictive maintenance, and passenger seating behavior, comprising the steps:
    measuring the change in at least one parameter selected from temperature, pressure and/or strain by the sensor unit disposed in the cushion according to claim 1, wherein the parameter change is exerted/caused by a passenger sitting on the seat cushion;
    processing the measured data in the at least one processing unit and storing the data in the at least one storage unit of the management system, and
    displaying the processed data on the at least one display unit.

17. A cushion for an aircraft seat, comprising:
    at least one pad having an upper side and a lower side made of at least one plastic foam;
    at least one sensor system, the at least one sensor system being arranged in a region of the pad adjacent to the lower side of the pad; and
    at least one flame protection fabric covering at least one side, preferably the upper side of the at least one pad, and
    at least one cover on the upper side of the flame protection fabric,
    wherein a further sensor system is provided in the at least one cover.

* * * * *